(12) United States Patent
Cohn

(10) Patent No.: US 7,717,844 B2
(45) Date of Patent: May 18, 2010

(54) METHOD AND APPARATUS FOR STABILIZATION AND POSITIONING DURING SURGERY

(75) Inventor: William E. Cohn, Houston, TX (US)

(73) Assignee: Apaxis Medical, Inc., Houston, TX (US)

( * ) Notice: Subject to any disclaimer, the term of this patent is extended or adjusted under 35 U.S.C. 154(b) by 44 days.

(21) Appl. No.: 11/770,254

(22) Filed: Jun. 28, 2007

(65) Prior Publication Data

US 2008/0009668 A1    Jan. 10, 2008

Related U.S. Application Data

(60) Provisional application No. 60/806,670, filed on Jul. 6, 2006.

(51) Int. Cl.
*A61F 2/00* (2006.01)
(52) U.S. Cl. ...................................... 600/37
(58) Field of Classification Search ............. 600/16, 600/17, 37, 201, 227–229, 206; 128/897
See application file for complete search history.

(56) References Cited

U.S. PATENT DOCUMENTS

| 6,019,722 | A   | 2/2000  | Spence et al. |
|-----------|-----|---------|---------------|
| 6,319,231 | B1  | 11/2001 | Andrulitis |
| 6,390,976 | B1* | 5/2002  | Spence et al. ............... 600/210 |
| 6,610,071 | B1  | 8/2003  | Cohn et al. |
| 6,652,485 | B1  | 11/2003 | Gaudoin et al. |
| 6,676,597 | B2  | 1/2004  | Guenst et al. |
| 6,682,505 | B2  | 1/2004  | Bates et al. |
| 6,758,809 | B2  | 7/2004  | Briscoe et al. |
| 6,769,434 | B2  | 8/2004  | Liddicoat et al. |
| 6,790,231 | B2  | 9/2004  | Liddicoat et al. |
| 6,860,892 | B1  | 3/2005  | Tanaka et al. |
| 6,866,628 | B2  | 3/2005  | Goodman et al. |
| 7,048,681 | B2  | 5/2006  | Tsubouchi et al. |

(Continued)

OTHER PUBLICATIONS

Collart, Frederic et al., "A safe, alternative technique for off-pump left ventricular assist device implantation in high-risk reoperative cases," Online at: http://icvts.ctsnetjournals.org/cgi/content/full/3/2/286, Interactive Cardiovascular and Thoracic Surgery 3, 2004, pp. 286-288.

(Continued)

*Primary Examiner*—Charles A Marmor, II
*Assistant Examiner*—Christine D Hopkins
(74) *Attorney, Agent, or Firm*—Conley Rose, P.C.

(57) ABSTRACT

Novel surgical devices for off-pump surgery are described herein. The disclosed apparatus employs a novel suction element that releasably couples to a surgical connector. In an embodiment, a surgical device comprises a suction element adapted to be releasably coupled to a surgical connector. The suction element has an opening for stabilizing said surgical connector against the surface of an organ by suction. The surgical device further comprises a flexible arm connected to the suction element. The flexible arm is capable of being fixed in a stationary position to hold the surgical connector and the organ in place. The novel suction element in combination with a flexible arm not only positions and stabilizes an organ during surgery, but also positions and stabilizes the surgical connector on the organ during a surgical procedure such as an LVAD implantation.

22 Claims, 11 Drawing Sheets

U.S. PATENT DOCUMENTS

| | | |
|---|---|---|
| 2004/0019299 A1 | 1/2004 | Ritchart et al. |
| 2004/0030348 A1 | 2/2004 | Peterson et al. |
| 2004/0059280 A1 | 3/2004 | Makower et al. |
| 2004/0068217 A1 | 4/2004 | Hindrichs et al. |
| 2004/0138522 A1* | 7/2004 | Haarstad et al. ............... 600/37 |
| 2005/0215851 A1* | 9/2005 | Kim et al. .................... 600/37 |
| 2006/0135984 A1 | 6/2006 | Kramer et al. |

OTHER PUBLICATIONS

Patent Cooperation Treaty International Search Report and Written Opinion dated Sep. 23, 2008 for International Application No. PCT/US07/72759, 3 pages.

* cited by examiner

METHOD AND APPARATUS FOR STABILIZATION AND POSITIONING DURING SURGERY

CROSS-REFERENCE TO RELATED APPLICATIONS

This application claims benefit of U.S. Provisional Application Ser. No. 60/806,670, filed Jul. 6, 2006, and entitled "Surgical Tools for LVAD Implantation," which is incorporated by reference in its entirety.

BACKGROUND

1. Field of the Disclosure

This disclosure relates to generally to the field of surgery. More specifically, the disclosure relates to devices for off-pump surgery.

2. Background of the Invention

Over 3.4 million people die each year because of congestive heart failure, a condition that often cannot be treated with drug or surgical therapies. For most patients that suffer heart failure, the best option is heart transplantation via an organ donor or by artificial means. The scarcity of suitable donor hearts (<2,000 per year) has left patients and doctors with no choice but to look to artificial heart therapies. This has been a prime motivating factor in the development of a total artificial heart (TAH). Although a reliable TAH has yet to be developed, great strides have been made in the development of implantable left ventricular assist devices (LVADs). Instead of totally replacing heart function, an LVAD supports the failing left ventricle by pumping blood from the left atrium or ventricle into the systemic circulation. LVADs have provided a well accepted means of stabilizing patients with heart failure until an acceptable donor has been procured.

Although current volume displacement or pulsatile LVADs have performed well clinically, their reliability after 18 months or so has been poor due to mechanical wear. These pumps utilize a pusher plate or diaphragm as well as inlet and outlet valves that result in pulsatile ejection not unlike the human heart. A pump that ejects 80 times per minute must eject 42 million times a year which presents a prohibitive design challenge for a mechanical system. As such, there has been interest in developing new types of pumps that do not rely on cyclic mechanical actuation. These efforts have resulted in the development of continuous flow pumps.

Continuous flow pumps offer several advantages over pulsatile pumps. Continuous flow pumps are generally smaller than pulsatile pumps and are more energy efficient. There is only one moving part, and many designs have no bearings or other components that are subject to mechanical wear. In addition, continuous flow pumps have the intrinsic ability to adjust pump output based on inflow and outflow pressure. These features make continuous flow pumps less likely to fail over time, and better suited for implantation in smaller patients.

A typical LVAD implantation procedure typically requires coring about a 2 cm hole in apex of the left ventricule. Before the apical hole is cored, the heart is elevated into position with laparatomy pads. The surgeon then cores the hole into the apex of the heart using either a coring tool or a scalpel. The surgeon then sutures an apical LVAD connector or cuff at the desired location on the ventricle such that a fluid tight connection is made. Once the LVAD connector is securely sutured to the left ventricle, the surgeon attaches the LVAD to the LVAD connector.

Traditionally, the patient is connected to a heart-lung machine, usually referred to as cardiopulmonary bypass, during the implantation procedure. Since the patient's blood is bypassed to the heart-lung machine, the pressure inside the left ventricle is significantly reduced. Thus, when the surgeon cores the hole from the left ventricular apex, minimal blood loss occurs and the surgeon has sufficient time to insert the LVAD's cannula into the LVAD connector.

However, though well tolerated by most patients, cardiopulmonary bypass constitutes a significant risk in the very ill and the very elderly. In patients with pre-existent organ dysfunction including organic brain disease, hepatic cirrhosis, renal insufficiency, and pulmonary insufficiency, CPB can cause significant morbidity or death. As patients with advanced heart failure not infrequently have co-morbid illnesses, avoiding cardiopulmonary bypass during LVAD insertion is attractive. As such, doctors have begun exploring surgical techniques without the use of the heart-lung machine i.e. off-pump surgery.

Off-pump LVAD implantation, however, presents substantial difficulties. For example, the surgeon is faced with the difficult task of operating on a moving heart. Further, the ventricle is positioned in the chest cavity behind the left breastbone. Repositioning the heart to make the ventricle more accessible while still permitting the heart to beat is not an easy task. Moreover, once positioned properly, the beating ventricle must be steadied in order to precisely suture the apical cuff or connector in place.

Coring a hole in the ventricle during off-pump surgery poses even greater difficulties. Because the patient is not on cardiopulmonary bypass, the heart is still responsible for maintaining the circulation. As such, the heart fills completely, generates high wall tension and cavity pressure, and ejects with each cardiac systole. Only by coring the apical plug in one swift move and inserting a finger, a plug, or the LVAD, can exsanguinating hemorrhage be averted and cardiac output maintained.

Another disadvantage to current off-pump surgical techniques is that it is difficult to ensure that the excised/cored heart tissue has been completely removed from the ventricle. For example, present surgical devices use an anvil in conjunction with a coring tool. These devices require making a cruciate incision in the ventricle and then inserting the anvil into the ventricle. Such a device not only causes unnecessary bleeding, but also does not provide an effective means of ensuring the complete removal of tissue.

Consequently, there is a need for surgical tools which allow a surgeon to implant ventricular assist devices without the use of a heart-lung machine i.e. off-pump. The surgical tools preferably should be simple to use and should minimize additional blood loss.

BRIEF SUMMARY

Novel surgical tools for off-pump surgery are described herein. The disclosed apparatus employs a suction element that is adapted to releasably couple to a surgical connector. The novel suction element in combination with a flexible arm not only positions and stabilizes an organ during surgery, but also positions and stabilizes the surgical connector on the organ. The flexible arm is capable of being locked into place to hold the connector and organ in place during a surgical procedure such as an LVAD implantation. Further features of embodiments of the apparatus are described below.

In an embodiment, a surgical device comprises a suction element adapted to be releasably coupled to a surgical connector. The suction element has an opening for stabilizing the surgical connector against the surface of an organ by suction. The surgical device further comprises a flexible arm connected to the suction element. The flexible arm is capable of being fixed in a stationary position to hold the surgical connector and the organ in place.

In a further embodiment, a surgical device comprises a surgical connector. The surgical device also comprises a suction element releasably coupled to the surgical connector. The suction element has an opening for securing the surgical connector to the surface of an organ by suction. Moreover, the surgical device comprises a flexible arm connected to the suction element. The flexible arm is capable of being locked into a fixed position to stabilize the surgical connector and the organ.

In another embodiment a method comprises providing a surgical device comprising a flexible arm capable of being locked into a fixed position and said flexible arm attached to a suction element. The suction element is releasably coupled to an apical ventricular assist device connector. The method further comprises applying a vacuum to the suction element. Moreover, the method comprises positioning the suction element releasably coupled to the surgical connector on to the surface of an organ. The surgical connector and the organ are held in place by the vacuum from the suction element. In addition, the method comprises locking said flexible arm in place to stabilize the organ and the surgical connector.

The disclosed device offers several advantages over existing technologies. These technologies often require two devices to position and stabilize an organ such as the heart. That is, one device is required to position the organ while a second device is used to stabilize the target area of the organ to be operated on. In addition, prior art solutions do not provide means for positioning or stabilizing the actual implants or surgical connectors on to the target organ. The disclosed apparatus performs all the above functions in one simple device.

The foregoing has outlined broadly the features and technical advantages of the invention in order that the detailed description of the invention will be described hereinafter that form the subject matter of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ".

DETAILED DESCRIPTION OF THE PREFERRED EMBODIMENTS

Novel surgical tools for off-pump surgery are described below. As defined herein, off-pump surgery refers to any surgical procedure performed without the assistance of a heart-lung machine i.e. cardiopulmonary bypass. However, the disclosed surgical tools and methods may also be used for surgeries that utilize cardiopulmonary bypass.

Surgical Device for Positioning and Stabilizing an Organ

Figure 1:
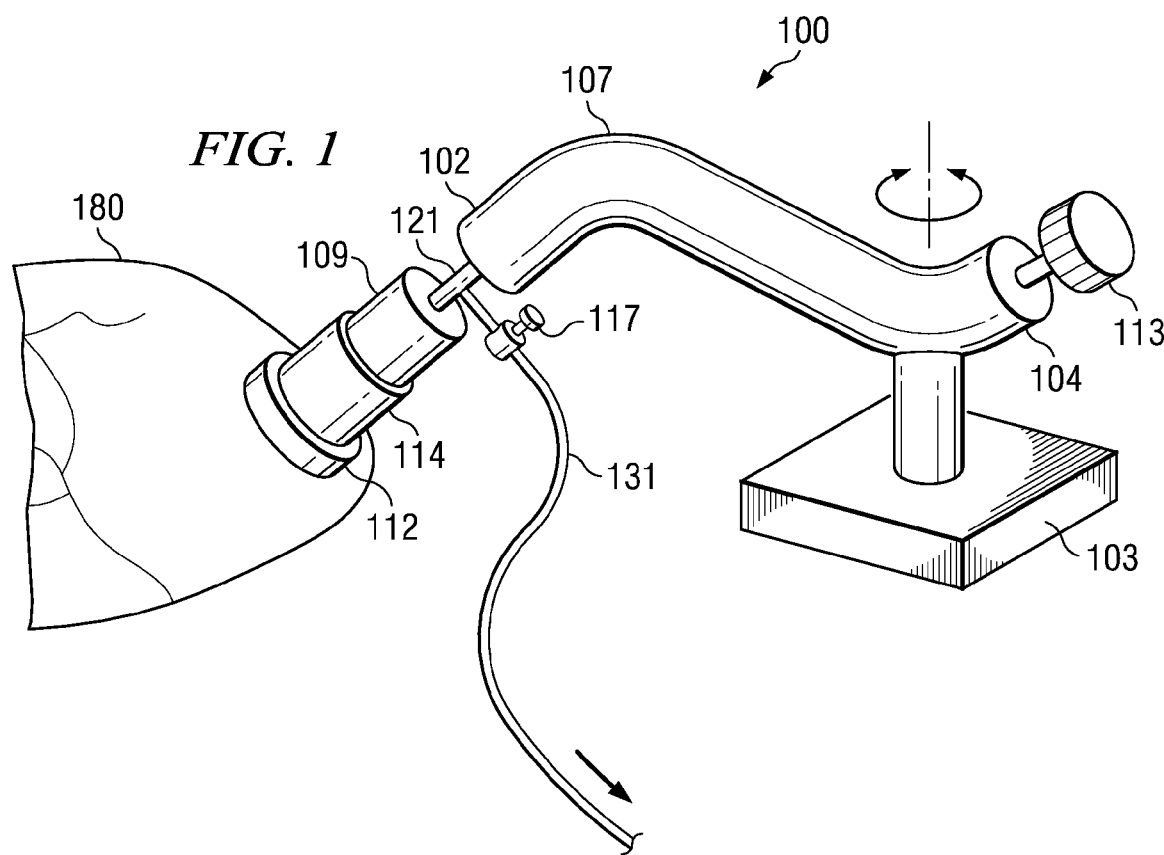
FIG. 1 illustrates an embodiment of a surgical device for positioning and stabilizing both a surgical connector and an organ.

FIG. 1 illustrates an embodiment of a surgical device for positioning and stabilizing an organ. In an embodiment, the apparatus comprises an arm 107, a base 103, and a suction element 109. The arm 107 has a distal end 102 and a proximal end 104. Arm 107 is coupled to a stabilizing base 103 to secure the arm 107. Arm 107 may be rotatable about the base 103 to provide further positioning for the surgeon. Stabilizing base 103 preferably comprises a clamp or fastener to secure apparatus to a surgical retractor or some other solid support. Distal end 102 of arm 107 is coupled to a suction element 109.

Suction element 109 is generally hollow and has an opening at its distal end so that air may be sucked through the suction element 109 to create a vacuum or suction. The suction from suction element 109 serves to stabilize or hold an organ in place and also to facilitate connection of an implant to the organ. In a further embodiment, the distal or organ-contacting opening of the suction element 109 is adapted to conform to the surface of a specific organ. For example, in at least one embodiment, suction element 109 is adapted to fit over the apical portion of the left ventricle 180 of a heart.

In an embodiment, suction element 109 is coupled to the arm 107 in such a way as to extend longitudinally away from distal end of arm 107. For example, suction element 109 may be attached or connected to flexible arm 107 by a hollow member 121. Hollow member 121 is preferably in fluid communication with suction element 109. In another embodiment, a joint is disposed between hollow member 121 and distal end of arm 107 (not shown). In other words, hollow member 121 is connected to arm 107 by the joint. The joint provides further articulation for the arm 107 and allows easier positioning of the suction element over the organ. Any suitable joint may be utilized for this purpose including without limitation, hinges, ball joints, swivel joints, and the like.

In an embodiment, a vacuum line 131 is connected directly to suction element 109 to pull a vacuum within the suction element 109. In another embodiment, vacuum line 131 is attached to hollow member 121. Alternatively, vacuum line 131 is run coaxially through arm 107 (not shown). The vacuum line 131 is typically connected to the vacuum connection available in any standard operating room. In a further embodiment, a valve 117 is disposed between the vacuum line and suction element. Valve 117 may be any suitable device used to regulate the vacuum.

In preferred embodiments, suction element 109 is adapted to be releasably coupled to a surgical connector 114. Thus, the suction element 109 not only positions and stabilizes an organ, but is also capable of simultaneously positioning and stabilizing various surgical connectors. The surgical connector 114 may be any connective device that is attached or sutured to an organ or a vessel (e.g. heart, liver, kidney, stomach, etc.) to form a connection between an artificial implant and an organ. Examples of suitable surgical connectors include without limitation, sleeves, grafts, cuffs, connectors, cannulas, and the like. Although such connectors are generally tubular in configuration, the surgical connector 114 may comprise any appropriate geometry suitable for surgical applications.

Figure 2:
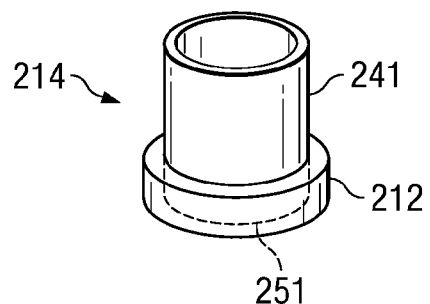
FIG. 2 illustrates a typical apical ventricular assist device connector.

In a preferred embodiment, the surgical connector 114 is an apical LVAD connector 214 as shown in FIG. 2. In general, the apical LVAD connector is used to guide and connect the inflow conduit of an LVAD with the left ventricle of the heart. The apical LVAD connector 214 has a hollow body 241 having a heart-contacting end 251. Heart-contacting end 251 is circumferentially surrounded by a suture or sewing cuff 212. The surgeon sutures or stitches this cuff 212 to attach the connector 214 to the heart in water-tight fashion. Generally, the LVAD connector 214 is tubular in configuration. However, the LVAD connector may comprise any suitable geometry such as rectangular, hexagonal, oval, etc In a preferred embodiment, suction element 109 is cylindrical or tubular in geometry. However, the suction element 109 may comprise any geometry such that it corresponds to a surgical connector. In tubular embodiments, suction element 109 is adapted to have diameter such that it slidingly fits within the surgical connector 114. Surgical connector 114 is therefore held securely in place by the tight fit e.g. friction fit, between connector 114 and suction element 109. Alternatively, suction element 109 may have a greater diameter than the surgical connector 114 such that suction element can be placed over surgical connector 114. In most embodiments, suction element 109 is adapted to releasably couple to existing surgical connectors in the marketplace.

In other embodiments, suction element 109 is configured or adapted to releasably couple to a surgical connector by any suitable connection means such as threaded or screw connections, snap-fit connections, bayonet connections, and the like. In such embodiments, it is envisioned that a surgical connector may be designed specifically for use with suction element 109.

In an alternative embodiment, suction element 109 is detachably attached to hollow member 121. Suction element 109 may be coupled to hollow member 121 with any suitable coupling. The coupling preferably creates an air tight seal between suction element 109 and hollow member 121 to maintain the necessary suction. Examples of suitable connections include without limitation, threaded connections, bayonet connections, etc. Thus, it is contemplated that a variety of suction elements 109 corresponding to different surgical connectors may be attached to arm 107. In further embodiments, suction element 109 is disposable and is replaced for each surgical procedure. In another embodiment, both hollow member 121 and suction element are detachable from arm 107.

Suction element 109 may be made of any suitable material. In preferred embodiments, suction element 109 is made of a polymeric material. Examples of suitable polymeric materials include without limitation, polypropylene, polyethylene, silicone, polyurethane, polycarbonate, or combinations thereof. In non-disposable embodiments of suction element 109, the material is preferably sterilizable or autoclavable. Such materials include without limitation, ceramics, glass, metal, or combinations thereof.

Arm 107 is preferably flexible and is capable of being locked in various positions. In an embodiment, arm 107 is segmented or articulated. Alternatively, arm 107 comprises a continuous tube or cylinder made from a polymeric material. By locking arm 107 into position, the user is able to stabilize the organ in a desired position for attaching a surgical connection. In an embodiment, arm 107 is locked into place by tension. User turns knob 113 attached to proximal end 104 of arm 107 to increase tension and lock arm 107 into place. However, arm 107 may be locked in place by any suitable means. In another embodiment, arm 107 is held in place merely by the nature of the material. For example, a non-resilient deformable material may be employed that is capable of holding its shape without tension or other means. Such materials may include without limitation, ductile metals, polymers, or combinations thereof. According to a preferred embodiment, arm 107 is tubular in configuration. However, arm 107 may have different cross-sections such as rectangular, triangular, hexagonal, etc.

Figure 3A:
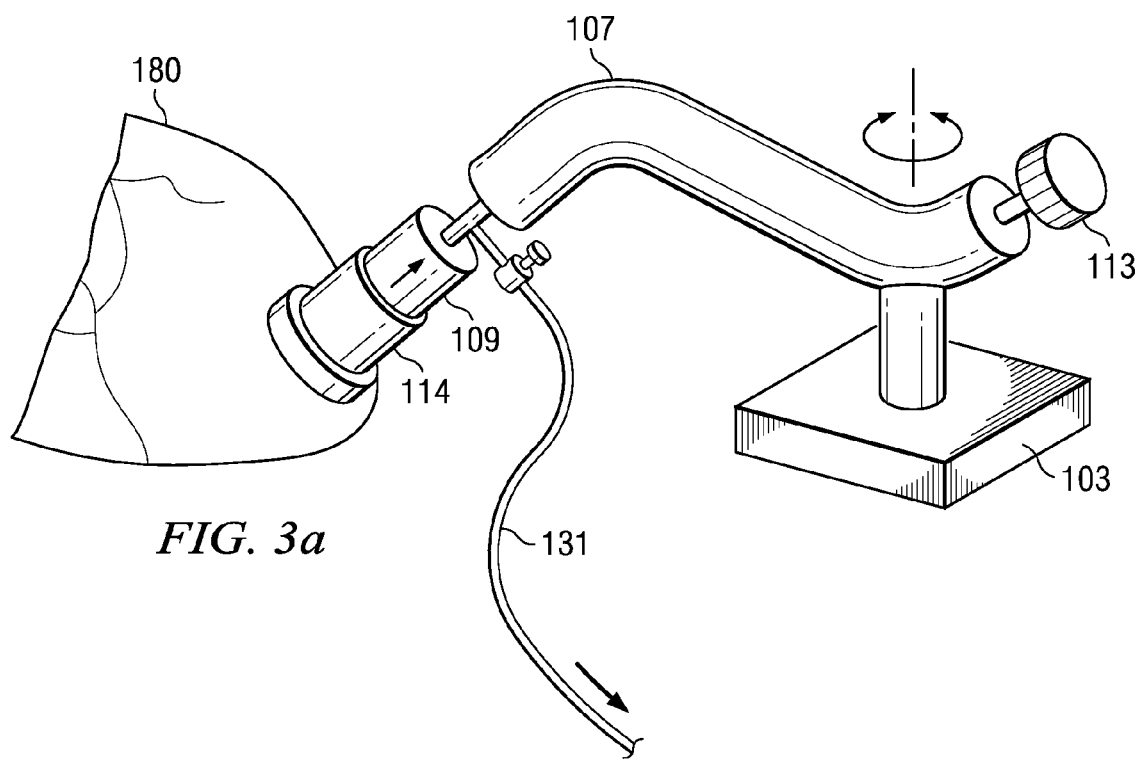
FIGS. 3a-d illustrates an embodiment of a method of positioning and stabilizing a surgical connector and an organ.

Referring now to FIGS. 3a-d, in a method of positioning and stabilizing an organ (e.g. the heart) during surgery, the base 103 is clamped to a secured platform (i.e. a surgical retractor or the surgical table) to hold apparatus 100 in place. Vacuum is continuously pulled from suction element 109 through the vacuum line. Valve 117 may be used to temporarily halt vacuum through suction element 109. Surgical connector 114 is typically already inserted on to distal end of suction element 109 with the suture ring 112 oriented away from suction element opening. The suction element 109 is then placed over the desired surgical site. Vacuum is re-applied and a portion of the organ surface is captured by suction element 109 via the force of the vacuum as shown in FIG. 3a.

Figure 3B:
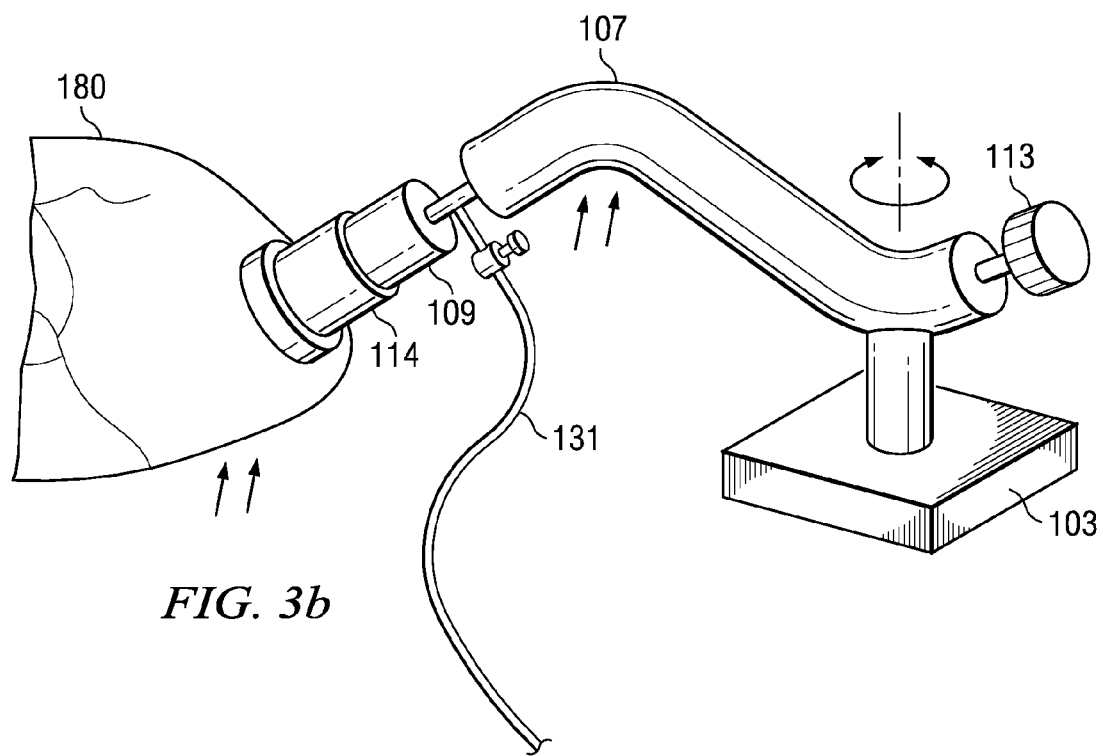

After the organ surface has been captured by suction element 109, the user (e.g. surgeon) may then move arm 107 into a desired position (FIG. 3b). As user moves arm 107, the organ 180 moves accordingly with the arm's movement. Thus, user can shift the organ to a desired stationary operating position without any bulky packing such as traditional laparotomy pads. Once the organ 180 is in position, the arm 107 is locked either by turning knob 113 or merely left in place because of the material properties of the arm 107. Once fixed, the organ's position may be indefinitely maintained until user chooses to move arm 107.

Figure 3C:
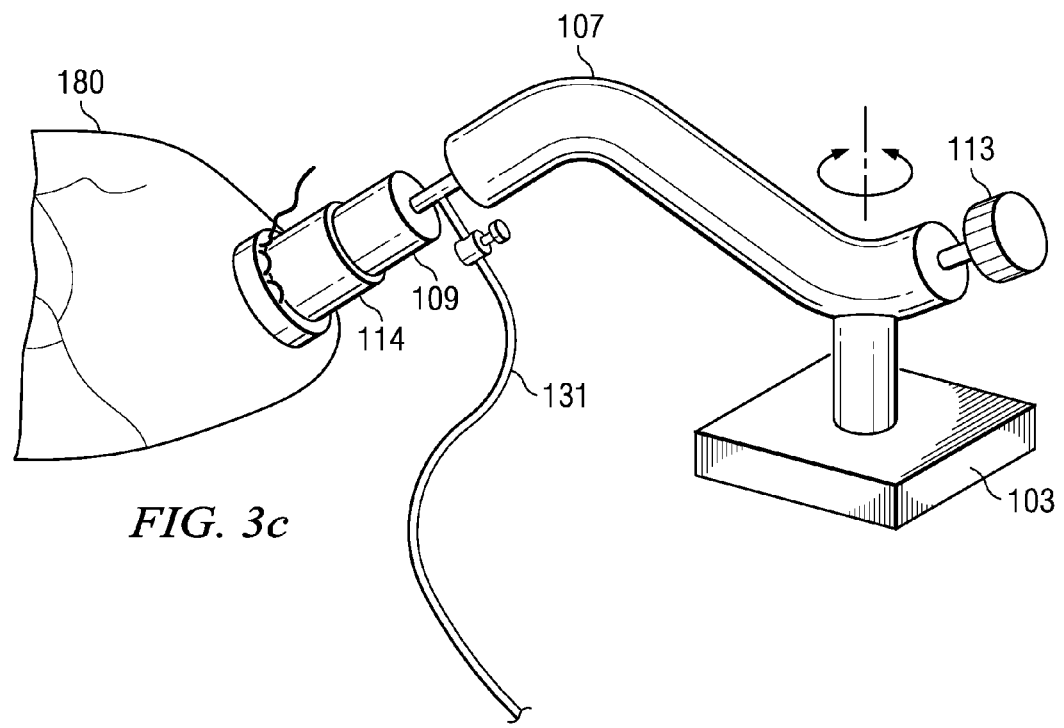

Not only does the disclosed apparatus 100 provide a means of positioning the organ, but it also stabilizes the organ surface during a surgical procedure. For example, during off-pump LVAD implantation, although the heart may be positioned properly, the ventricle is still beating at physiological pressure. As such, the surface of the ventricle is in constant motion, providing an unstable surface for surgeons. The vacuum being pulled through suction element 109 immobilizes the undulating surface of the organ. Furthermore, because surgical connector 114 is coupled to suction element 109, surgical connector 114 is also held in place against the surface of organ 180. As shown in FIG. 3c, the surgeon is now able to attach or suture the stabilized surgical connector 114 on to the surface of organ 180 without concern that the surgical connector 114 will shift during attachment or suturing.

In comparison, prior art surgical devices stabilize the organ, but do not provide a means of positioning and stabilizing a surgical connector (e.g. an LVAD connector) as it is fixed into place. Therefore, embodiments of the apparatus 100 provide a simple solution for stabilization and positioning of both the heart and the LVAD connector. It is envisioned that the above described methods and apparatus will not be limited to LVAD connectors and the heart, but may be used for other surgical connections and organs.

Figure 3D:
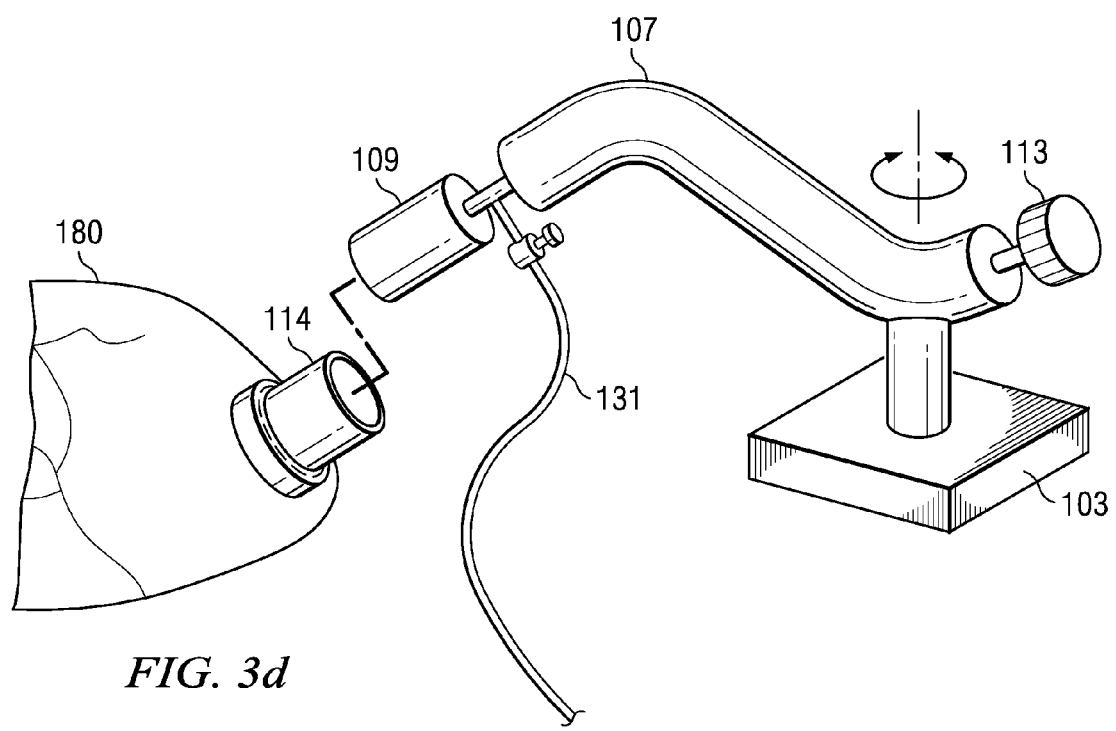

Once properly positioned and stabilized, the surgical connector 114 is attached to the organ surface via the connector's suture ring 112. When the user is finished attaching surgical connector 114 into place, the vacuum is disengaged and flexible arm 107 may be unfixed from its stationary position (FIG. 3d). Suction element 109 is de-coupled from surgical connector 114 and organ 180, leaving surgical connector 114 attached to organ 180.

Organ Coring Tool and System

Figure 4:
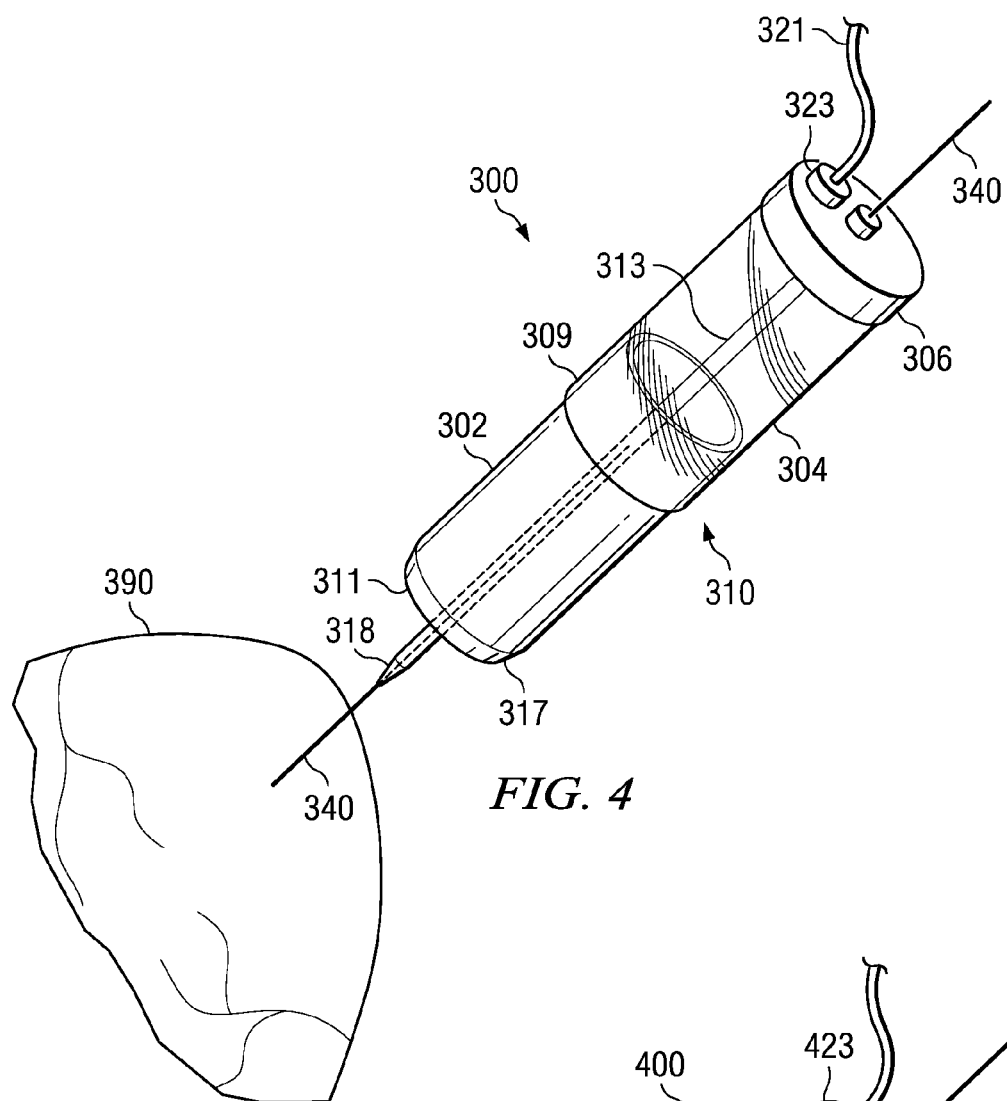
FIG. 4 illustrates an embodiment of a surgical coring tool.

Tools and systems for coring an organ are described herein. In a specific embodiment, the organ is a heart. However, other organs may be cored using embodiments of the disclosed system. The system allows a surgeon to form a hole in an organ such as without causing a significant amount of blood loss. Furthermore, the system ensures that all excised heart tissue is removed, leaving no remnants within the heart chamber. In an embodiment, the system includes a coring tool 300, a balloon catheter, and a guide wire 340. FIG. 4 illustrates an embodiment of a coring tool 300 that is used as part of the off-pump system. Coring tool 300 and balloon catheter both are longitudinally coaxial to guide wire. Generally, coring tool 300 has a hollow body 310. In preferred embodiments, hollow body 310 has a coring portion 302, a vacuum chamber 304, and an inner elongate member 313. Coring portion 302 and vacuum chamber 304 of coring tool are preferably hollow. In an embodiment, an outer guard (not shown) wraps around the outer surface of coring tool 300 and slides along the longitudinal length of coring tool 300. In general, coring portion 302 is forced into the desired portion of the organ to be cored. The cored tissue is pulled into vacuum chamber 304 by suction force. As will be described in more detail below, the opening created by the coring tool 300 may be blocked by the balloon portion of a balloon catheter.

Figure 5:
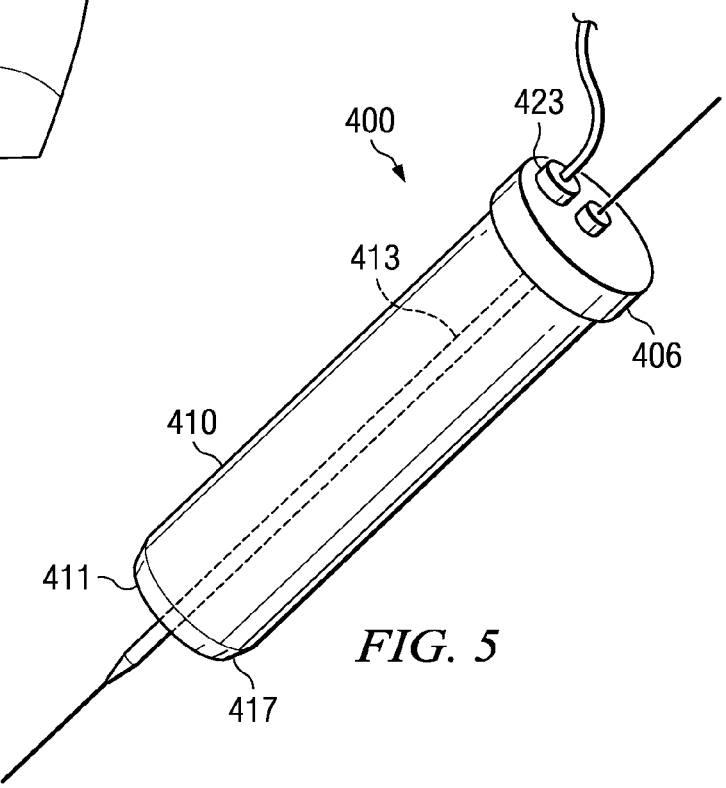
FIG. 5 illustrates another embodiment of surgical coring tool.

Referring now to FIG. 5, in an embodiment, coring portion and vacuum chamber are integral to each other such that they form a single hollow body 402. In other words, it is contemplated that coring tool need not be separable into two separate portions (i.e. coring portion 302 and vacuum chamber 304), but may comprise a uniform hollow body 402 with an open distal end 411 and a closed proximal end 406. Open distal end 417 has a cutting edge 411. Closed proximal end 406 has a vacuum connection 423, although vacuum connection 423 may also be located along hollow body 402.

Hollow body 402 is preferably made of a translucent or transparent plastic to allow the user to visualize any excised tissue in hollow body lumen. However, in some embodiments, hollow body 402 is made of metal or other suitable material. Examples of suitable materials include without limitation, polycarbonate, polystyrene, polyethylene, polypropylene, glass, stainless steel, or combinations thereof.

Referring back to FIG. 4, according to a preferred embodiment, coring portion 302 is tubular in configuration in order to cut a circular hole into an organ and is disposed distal to vacuum chamber 304. However, coring portion 302 may have any suitable cross-section for other purposes. Coring portion 302 has a cutting edge 311 at open distal end 317 of hollow body 310. Cutting edge 311 is preferably sharpened or tapered to easily bore through the heart tissue. As will be described further below, proximal end of coring portion 302 is adapted to fit into vacuum chamber 304 or be attached to vacuum chamber 304. In an embodiment, the outer surface of cutting edge 311 is beveled while the inner surface is straight or non-beveled as shown in FIG. 4. In addition, the inner surface of coring portion 302 may be flush with inner surface of vacuum chamber 304 to allow the excised tissue to pass through to vacuum chamber 304.

In a preferred embodiment, coring portion 302 is made of metal such as surgical steel to easily penetrate into the heart tissue. However, any suitable materials may be used to construct coring portion. For example, coring portion 302 may comprise a hard plastic or a polymeric material. It is envisioned that coring portion 302 may be re-usable and sterilizable. Alternatively, coring portion 302 may be disposable. In addition, coring portion 302 may be of any length in respect to vacuum portion.

Vacuum chamber 304 of coring tool is also hollow and typically has the same cross-sectional geometry as coring portion 302. Proximal end of vacuum chamber 304 comprises closed proximal end 306 of hollow body 310 and is open at its distal end. In some embodiments, a vacuum line 321 is attached to the closed end of vacuum chamber 304 via a vacuum connection 323. Alternatively, vacuum connection 323 is located along the outer surface of vacuum chamber 304. Vacuum connection 323 may comprise a valve (not shown) to adjust the vacuum being pulled in hollow body 310. Optionally, a valve (not shown) is disposed between vacuum line 321 and closed end 306 of vacuum chamber 304 to regulate vacuum. For example, a simple stopcock (not shown) may be employed to turn vacuum on or off.

In a preferred embodiment, the open distal end of vacuum chamber 304 is adapted to receive coring portion 302 as seen in FIG. 4. Vacuum chamber 304 has a diameter that is greater than the diameter of the coring portion 302. Thus, in an embodiment, coring portion 302 is insertable into the lumen of vacuum chamber 304 and is press-fit into place. In further embodiments, coring portion 302 may be attached to vacuum chamber 304 by any suitable connection such as threaded connections, bayonet connections, snap-fit connections, and the like. Coupling between vacuum chamber 304 and coring portion 302 preferably forms an air tight seal capable of holding vacuum. In an alternative embodiment, vacuum chamber 304 has a diameter that is less than the diameter of the coring portion 302 such that vacuum chamber 304 is insertable into the lumen of coring portion 302.

In a preferred embodiment, vacuum chamber 304 is transparent or translucent enabling a user to see the excised heart tissue as it is sucked into vacuum chamber 304. Vacuum chamber 304 is preferably made of a polymeric material. Any suitable polymeric material may be used that is capable of being sterilized and is biocompatible. In an embodiment, vacuum chamber 304 is also disposable. Thus, in at least one embodiment, the vacuum chamber 304 and the coring portion 302 are both disposable.

Referring to FIG. 5, coring tool 300 further comprises an inner elongate member 413. In embodiments with a unitary hollow body, the inner elongate member 413 is disposed coaxially within hollow body 410. In embodiments with a two-part hollow body as seen in FIG. 4, the elongate member 313 is disposed coaxially within vacuum chamber 304 and coring portion 302. Proximal end of member 313 is attached to the proximal closed end 306 of hollow body 310 and extends longitudinally through the center of the hollow body lumen through the open distal end 317 of hollow body 310. Further, inner elongate member 313 is hollow and is longitudinally coaxial with guide wire 340.

In one embodiment, inner elongate member 313 is extendible and retractable, thus allowing the distance of the member's distal tip 318 past cutting edge 311 to be adjusted according to the thickness of the organ tissue. For example, inner elongate member 313 may be telescopic. Furthermore, elongate member 313 may extend through proximal closed end 306 of hollow body 310.

Inner elongate member 313 serves several purposes. First, it guides coring tool 300 along guide wire 340 and maintains the coring tool's trajectory to the target heart tissue to be excised. The inner diameter of inner elongate member 313 is slightly greater than the guide wire diameter so that coring tool 300 precisely slides along guide wire to intended excision site. In addition, inner elongate member 313 also impales and secures the heart tissue to prevent any excised tissue from remaining in the heart chamber. Distal end 318 of elongate member 313 preferably comprises a "snout" or bullet shape. Alternatively, distal end 318 of elongate member 313 is a sharpened tip. However, distal end 318 may comprise any configuration suitable to easily penetrate the heart chamber.

In at least one embodiment, vacuum chamber has a handle (not shown) to assist the user in manipulating coring tool 300. The handle facilitates removal of the coring tool 300 along with the excised tissue from the organ. In a particular embodiment, proximal end of elongate member 213 extends through closed end of hollow body 310 to form a handle. Alternatively, a handle may be attached to the outer surface of hollow body 310 or vacuum chamber 304.

According to a preferred embodiment, inner elongate member 313 extends through opening, past distal opening 317 of coring portion 302. This extension further allows elongate member 313 to act as a spacer between the cutting edge of coring tool 300 and balloon catheter. The spacer function prevents cutting edge from contacting the balloon catheter as coring tool 300 bores into the heart. As inner elongate member 313 penetrates through the heart wall, it pushes against the tip of balloon catheter and thus, forces balloon away from cutting edge.

Inner elongate member 313 is preferably made of a semi-rigid material such as a polymer. However, any suitable materials known to those of skill in the art to make catheters may be used. Examples of suitable polymers include polyethylene, polypropylene, PET, or combinations thereof. Alternatively, inner elongate member may be made of metal.

In another embodiment, coring tool 300 comprises an outer guard (not shown). As mentioned above, outer guard circumferentially surrounds coring tool 300. It is capable of sliding along the length of coring tool 300 over cutting edge even past the tip of inner elongate member 318. The purpose of the outer guard is to maintain a closed continuous passage as cored heart tissue is sucked into coring tool and coring tool is extracted from the heart. The outer guard prevents blood from escaping or spouting from the heart chamber in the time it takes balloon catheter to fill the newly formed hole in the ventricle.

Referring again to FIG. 5, in an embodiment, the coring device may comprise an inner hollow body (not shown) which is disposed coaxially within hollow body 402. Preferably, inner hollow body is tubular in geometry. In such an embodiment, vacuum is only applied through inner hollow body. Thus, vacuum connection 423 would be coupled to the proximal end of inner hollow body to provide suction through inner hollow body. In a further embodiment, inner hollow body may be retractable through closed proximal end 406. In cases where the organ tissue is thinner, the placement of the inner hollow body coaxially within hollow coring portion 302 may ensure that the cored tissue is captured within hollow body 402. In addition, inner elongate member 413 may be disposed coaxially within inner hollow body to provide guidance and further secure the excised tissue.

The guide wire 340 is any suitable wire known to those of skill in the art. According to one embodiment, guide wire 340 acts a guide through the heart wall, the heart chamber, aortic arch, and the femoral artery. An advantage of using guide wire 340 is that it serves as a guiding track for coring tool 300 and balloon catheter. Therefore, guide wire 340 ensures that coring tool 300 and balloon catheter are properly aligned.

Balloon catheter is adapted to be inserted into the heart chamber. Inflatable portion of balloon catheter is preferably inflatable to a diameter slightly greater than the diameter of coring portion 302. As will be described in more detail below, the larger diameter balloon plugs the hole created by the coring tool 300. Balloon catheter is made of any suitable biocompatible material. In other embodiments, balloon catheter is replaced with some other catheter device which is capable of plugging a hole in the heart chamber. Further embodiments of the balloon catheter are described below.

Figure 6A:
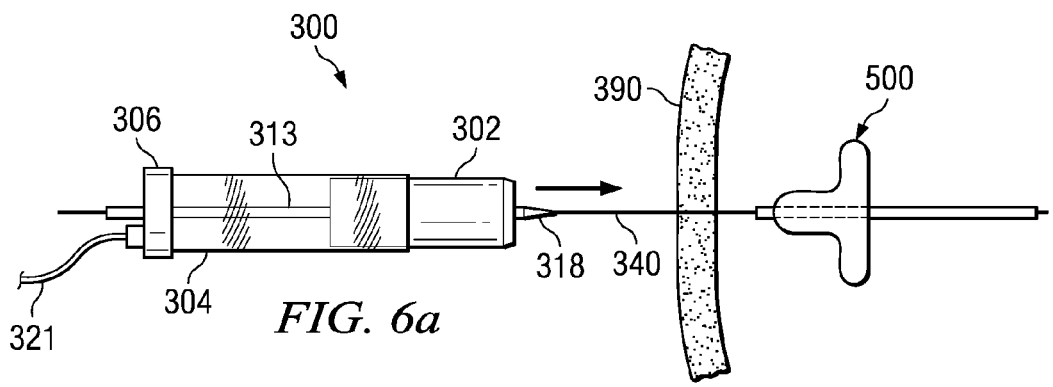
FIGS. 6a-c illustrates an embodiment of a method for coring an organ.
Figure 6B:
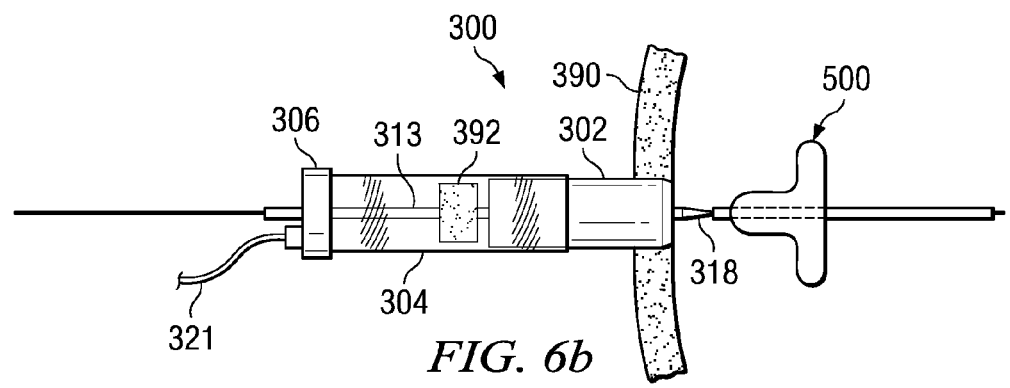
Figure 6C:
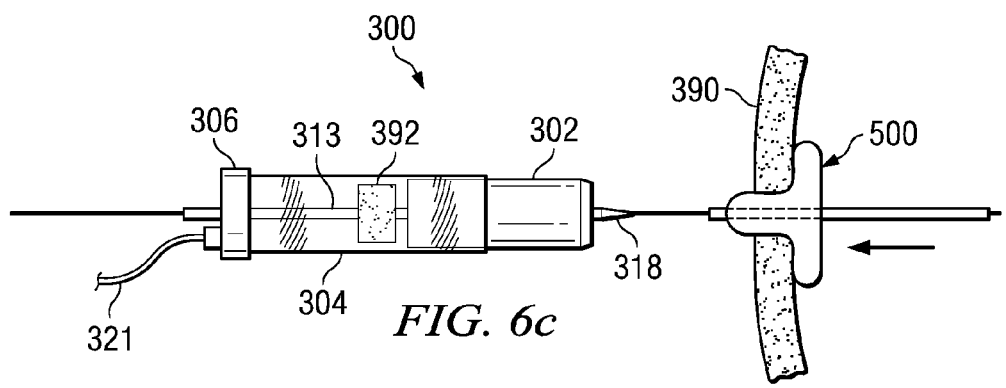

Referring now to FIGS. 6(a)-(c), in a method of coring a heart chamber, a guide wire 340 is attached to a needle. In an embodiment, prior to inserting a guide wire, the surgeon has attached an LVAD connector by techniques known to those of skill in the art or by the novel methods disclosed herein. The attached needle is then inserted into the target ventricle through the center of the LVAD connector. Because the heart is still pumping, the needle is automatically pumped through to the aorta. The needle and the guide wire navigate through the aortic arch and down the femoral artery. The user then extracts the needle from the femoral artery thereby forming a guide from the femoral artery all the way through the heart ventricle. A deflated balloon catheter is inserted through the femoral artery on to the guide wire. The guide wire serves as a track upon which the deflated balloon catheter rides as the user pushes the catheter up through the artery, through the aortic arch and back into the heart chamber. The balloon catheter is then inflated with contrast agent or any other suitable material.

Once guide wire 340 and balloon catheter are in place, coring tool 300 is then inserted on to guide wire 340 (see FIG. 6a). At this point, user may apply vacuum causing a pressure differential within the vacuum chamber 304 by turning a valve. User bores into heart chamber 390 with coring portion 302 until coring tool 300 penetrates into the interior of the heart chamber (see FIG. 6b). Furthermore, distal end 318 of elongate member 313 pierces heart chamber 390. The vacuum created by the pressure differential in the lumen of the coring tool 300 sucks the excised heart tissue into the lumen of the vacuum chamber 304. In embodiments where vacuum chamber 304 is transparent, surgeon can actually see when the excised heart tissue 392 enters the lumen of the vacuum chamber 304. Thus, the surgeon receives immediate visual confirmation that heart tissue has been completely resected. The inflated balloon catheter 500 plugs the tissue cavity formed by coring tool 300 by the outward pressure created by the beating heart when coring tool 300 is withdrawn from organ (see FIG. 6c). Thus, balloon catheter 500 acts as a plug to prevent the heart from spouting blood through the hole left by excision of heart tissue 392. In addition, balloon catheter 500 is a further measure to prevent excised heart tissue 392 from falling back into the ventricle. Elongate member 313 also serves to prevent heart tissue 392 from re-entering the heart chamber 390 as heart tissue 392 is securely impaled by elongate member 313.

After making sure that balloon catheter has securely plugged the newly formed hole, the surgeon can now insert an LVAD into the hole. Although, the coring method above has been described with respect to the heart, it is envisioned that the disclosed coring system may be used with other organs or blood vessels requiring resection of a defined portion of tissue such as bladder, stomach, liver, etc.

Automated Surgical Connector.

Figure 8:
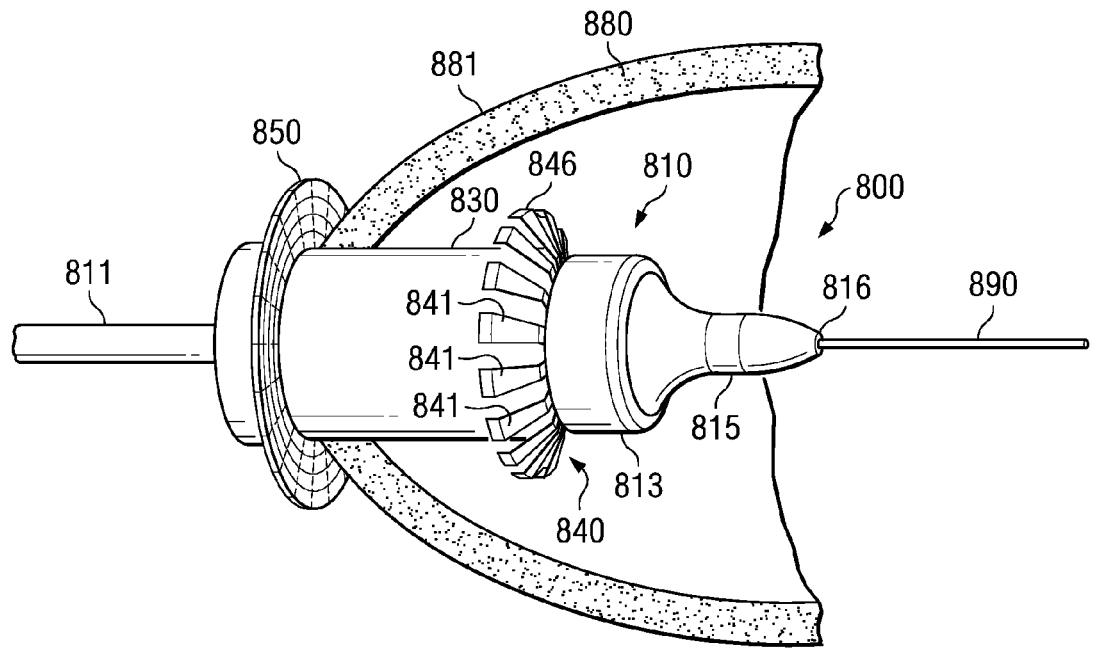
FIG. 8 illustrates an embodiment of a surgical connector in which the distal sealing member is shown without its fabric covering.

FIG. 8 illustrates an embodiment of an automated surgical connector 800. The disclosed connector obviates the need for positioning and suturing a surgical connector to an organ such as the heart. In addition, suturing calls for repeated penetration of an organ. The surgical connector 800 instead is held in place by a novel press-fit mechanism involving the force of sealing members pressed against the organ wall.

An embodiment of surgical connector 800 is illustrated in FIG. 8. In this embodiment, surgical connector 800 includes an inner body 810, an outer hollow body 830, a distal sealing member 840, and a proximal sealing member 850. Generally, inner body 810 is adapted to coaxially slide over a guide wire 890. Moreover, inner body 810 has a distal portion 815, a proximal portion 811 and a medial portion 813. Preferably, distal portion 815, proximal portion 811, and medial portion 813 form a continuous body. Furthermore, inner body 810 typically is circular in cross-section. However, inner body 810 may comprise any suitable cross-sectional geometry. In some embodiments, inner body 810 may be hollow. Alternatively, inner body 810 may be solid as long as a passage is provided within inner body to allow threading of a guide wire 890.

In at least one embodiment, medial portion 813 has a greater diameter than distal portion 815 and proximal portion 811. The transition from medial portion 813 to distal portion 815 is preferably tapered or contoured so as to provide a transition zone for the distal sealing member 840. In an embodiment, distal portion 815 has a blunt tip 816. Distal portion 815 may serve as a spacer between distal sealing member 840 and a balloon catheter in a guide wire coring system. In particular, blunt tip may be optimally configured so as to fit the outer surface of balloon catheter, further preventing any accidental puncture of the balloon.

Figure 9:
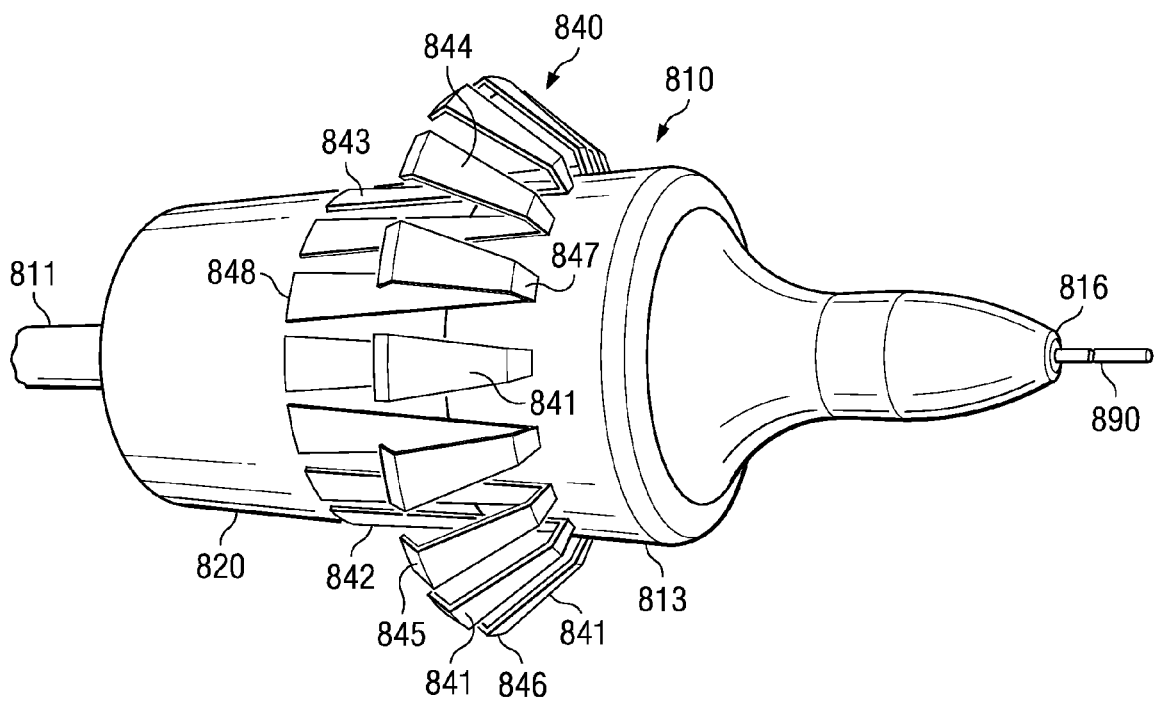
FIG. 9 illustrates an embodiment of a surgical connector without the outer hollow body and proximal sealing member.

In at least one embodiment, surgical connector 800 includes an intermediate sheath 820 as shown in FIG. 9. For illustrative purposes, FIG. 9 shows surgical connector 800 with only intermediate sheath 820, distal sealing member 840 and inner body 810. Intermediate sheath 820 is disposed around medial portion 813 of inner body 810 in between outer hollow body 830 and inner body 810. In most embodiments, intermediate sheath 820 is made of any suitable metal. However, other in other embodiments, intermediate sheath 820 may also be made of plastic. Furthermore, intermediate sheath 820 is typically slidably disposed around medial portion 813 of inner body 810. Thus, intermediate sheath 820 has a diameter that in only slightly greater than the diameter of medial portion 813. Intermediate sheath 820 serves to maintain distal sealing member 840 in its expanded position as will be described in more detail below.

According to an embodiment of a surgical connector 800, distal sealing member 840 comprises a support portion 842 and a sealing portion 846. Furthermore, the support portion 842 and sealing portion 846 together comprise a plurality of ribs 841. Each rib 841 has an axial portion 843 and a radial portion 844. Thus, axial portion 843 of each rib forms the framework or skeleton for support portion 842 while radial portion 844 of each rib 841 forms the framework for sealing portion 846. Axial portion 843 of each rib is preferably aligned along the longitudinal axis of inner body 810. In one embodiment, axial portion 843 of each rib 841 is tapered toward the distal end 847 of axial portion 843. The tapered axial portion 843 allows the distal sealing member 840 to expand or spread radially outward.

Radial portion 844 forms an angle with axial portion 843 and extends radially outward from axial portion 843. Radial portion 844 may form any suitable angle with axial portion 843. As with axial portion 843, radial portion 844 of each rib 841 may comprises a taper so as to accommodate expansion of distal sealing member 840. As shown in FIG. 9, radial portion 844 tapers from outer tip 845 to intersection of radial portion 844 with axial portion 843. Furthermore, in some embodiments, outer tip 845 of radial portion 844 is bent at an angle. The bent outer tip 845 facilitates compression of distal sealing member by outer hollow body 830. In yet other embodiments, outer tip 845 of radial portion 844 may overlap with the outer tips 845 of other ribs (not shown). This overlapping may allow for more compact compression of distal sealing member 840 in its compressed position.

Figure 10A:
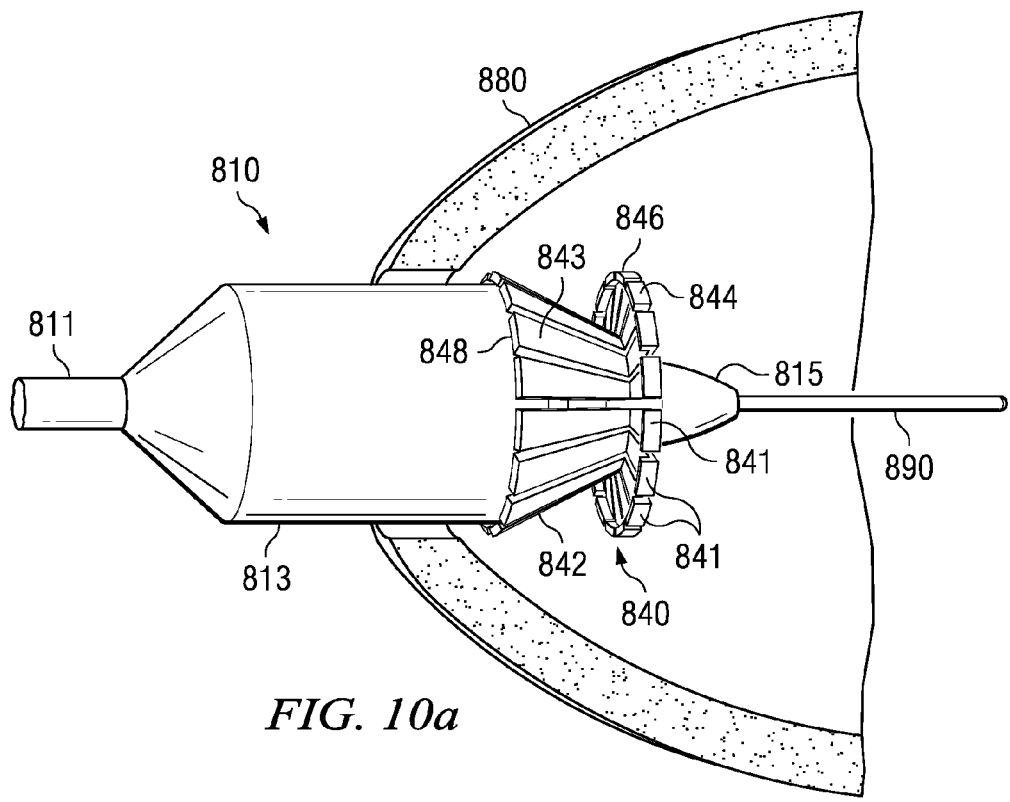
FIG. 10 illustrates the transition from the collapsed position of the distal sealing member to the expanded position of the distal sealing member.
Figure 10B:
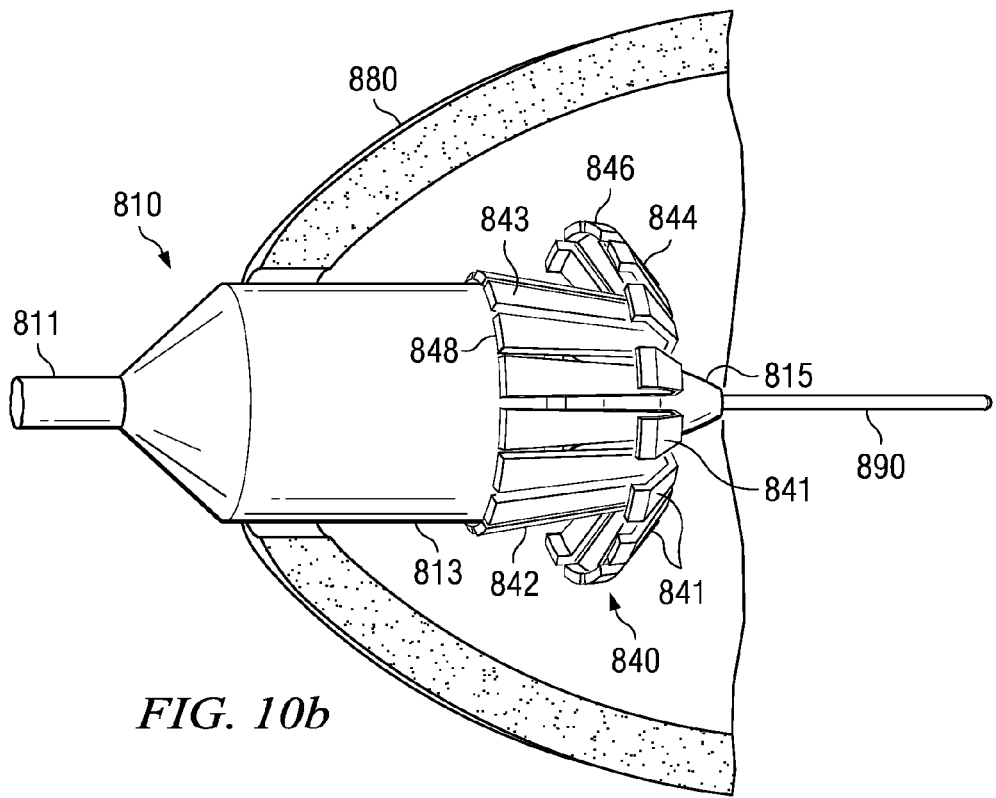
Figure 10C:
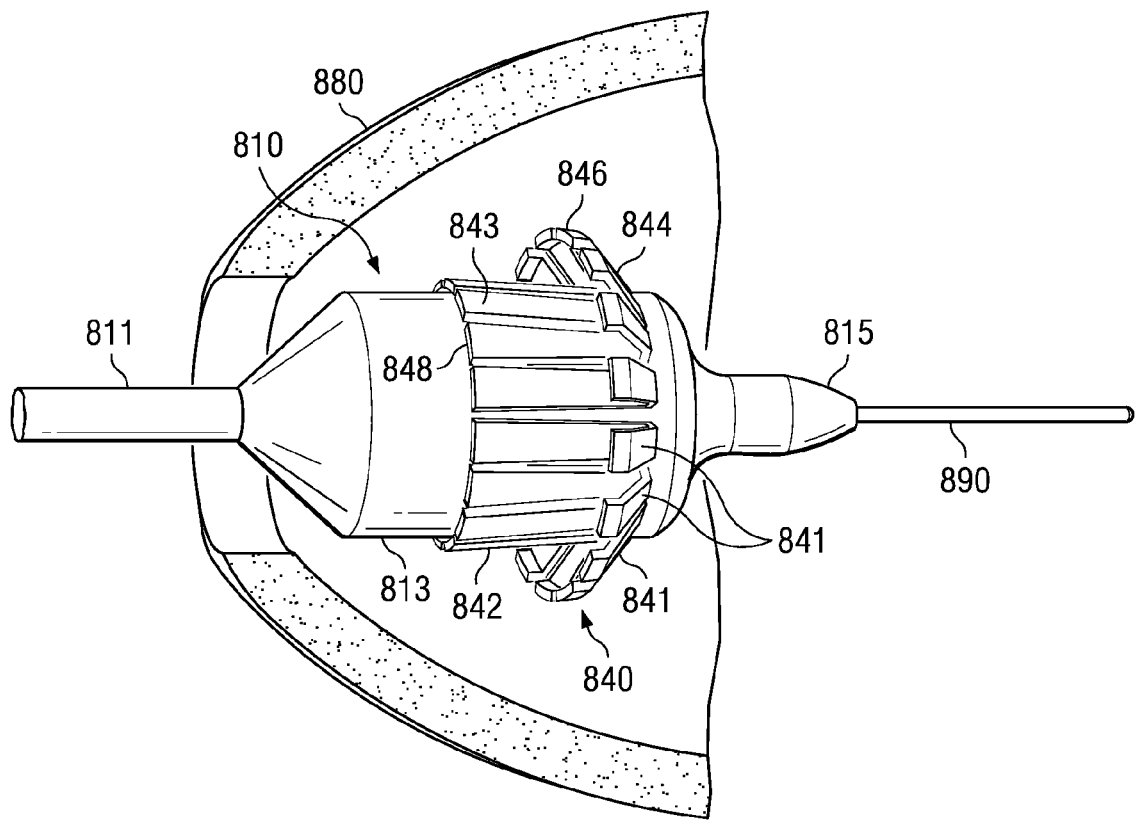

Distal sealing member 840 has a collapsed position and an expanded position as depicted in FIG. 10. FIG. 10 illustrates the transition from distal sealing member's 840 compressed position in FIG. 10A to its expanded position in FIG. 10C. In its compressed position, ribs 841 of distal sealing member 840 are contracted over distal portion of inner body 810. Thus, the taper in axial portion 843 and radial portion 844 of ribs 841 allow the ribs 841 to contract against each other. In some embodiments, axial portion 843 and radial portion 844 may be configured to overlap one another for further compression or contraction. Besides utilizing a tapered geometry for ribs 841, other geometries may be incorporated to optimize contraction of distal sealing member 840. For example, each axial portion 843 may comprise an angled portion (not shown).

As shown in FIG. 10A, the axial portions of ribs 841, when contracted, may form a frustroconical support portion 842 surrounding distal portion 815 of inner body 810. However, support portion 842 may comprise other configurations in order to conform to inner body 810 when compressed. In an embodiment, proximal end 848 of each axial portion 843 may be in contact with medial portion 813 of inner body 810 to begin the expansion of distal sealing member 840. As inner body 810 is pushed forward distally into organ 880, medial portion 813 spreads or forces axial portions 841 apart as illustrated in FIG. 10B. When medial portion 813 is completely inserted through frustroconical portion of distal sealing member, ribs 841 are completely spread or expanded into the expanded position of distal sealing member 840 in FIG. 10C.

In an embodiment, ribs 841 are planar in geometry. However, it is contemplated that ribs 841 may be of any geometry allows the ribs 841 to expand or collapse. For example, ribs 841 may also be cylindrical in cross-section e.g. wires. In preferred embodiments, ribs 841 are made of a non-thrombogenic metal. Generally, the metal is a resilient metal so as to impart spring-like properties to the ribs. Examples of suitable metals include without limitation, nitinol, copper, stainless steel, titanium, zinc, nickel, or combinations thereof. Distal sealing member 840 is also covered with a non-thrombogenic mesh or fabric. The mesh or fabric ensures the distal sealing member 840 forms a liquid tight seal with proximal sealing member. Specifically, the material may be a polymeric fabric made from polytetrafluoroethylene (PTFE), polypropylene, polyurethane, nylon, or combinations thereof. However, any suitable non-thrombogenic, biocompatible materials known to those of ordinary skill in the art may be used. An advantage of the disclosed connector over prior devices is that it does not have an inner cannula. Blood flowing from ventricle through connector will contact only the continuous surface of distal sealing member 840 and inner surface of intermediate sheath 820. These features lessen the chance of clots or thrombi forming in the heart.

Surgical connector 800 also comprises an outer hollow body 830. In an embodiment, inner body 810 is disposed coaxially within outer hollow body 830. Preferably, outer hollow body 830 has a diameter slightly greater than medial portion 813 of inner body 810. Outer hollow body 830 is disposed around intermediate sheath 820 and medial portion 813 of inner body 810. In addition, outer hollow body 830 slides along medial portion of inner body. Outer hollow body 830 may be made of any suitable material such as plastic or metal.

In a further embodiment, surgical connector comprises a proximal sealing member 850. As with distal sealing member 840, proximal sealing member 850 may also be comprised of a plurality of ribs (not shown) covered with a mesh or fabric as shown in FIG. 8. Although, it is not necessary for proximal sealing member 850 to be compressible and expandable, it is envisioned that certain embodiments may incorporate such a feature. Alternatively, proximal sealing member 850 comprises a solid and continuous piece of metal or plastic (not shown). According to at least one embodiment, proximal sealing member 850 is angled or contoured distally toward the distal end of inner body. Thus, the radial portions of the plurality of ribs which form the skeleton or frame of proximal sealing member are also angled distally. In addition, proximal sealing member is movably disposed around outer hollow body 830. Preferably, proximal sealing member is capable of being locked into position along outer hollow body 830. Any suitable mechanisms may accomplish this such as a threaded connection or ratchet mechanism between outer hollow body 830 and proximal sealing member. The mechanism allows the proximal sealing member 850 to move in a distal direction, but prevents the proximal sealing member from moving back in a proximal direction. In this way, organ or tissue is securely clamped between proximal sealing member and distal sealing member 840 to form a liquid tight or press-fit seal.

In a method, the described surgical connector 800 is used in conjunction with the coring system disclosed above. In an exemplary embodiment of the method, a guide-wire coring system, of which embodiments are described above, is used to create a hole in the organ. After the coring procedure, the balloon catheter remains in the newly created hole to prevent blood loss. However, it is contemplated that other coring procedures may be utilized in conjunction with embodiments of the surgical connector 800.

After a hole has been created in the organ 880, the surgeon then inserts inner body 810 over the guide wire 890 until distal tip 816 of inner body 810 contacts the balloon catheter (not shown). Distal end 816 of inner body 810 is preferably blunt to prevent puncture of balloon catheter. Using blunt tip 816 of distal end, the surgeon rapidly pushes balloon catheter back into the organ while inserting medial portion 813 of inner body 810 into the void or hole left by balloon catheter. As medial portion 816 has a diameter substantially equal to the diameter of the hole in the organ, insertion of medial portion prevents any loss of fluids from organ.

Figure 11A:
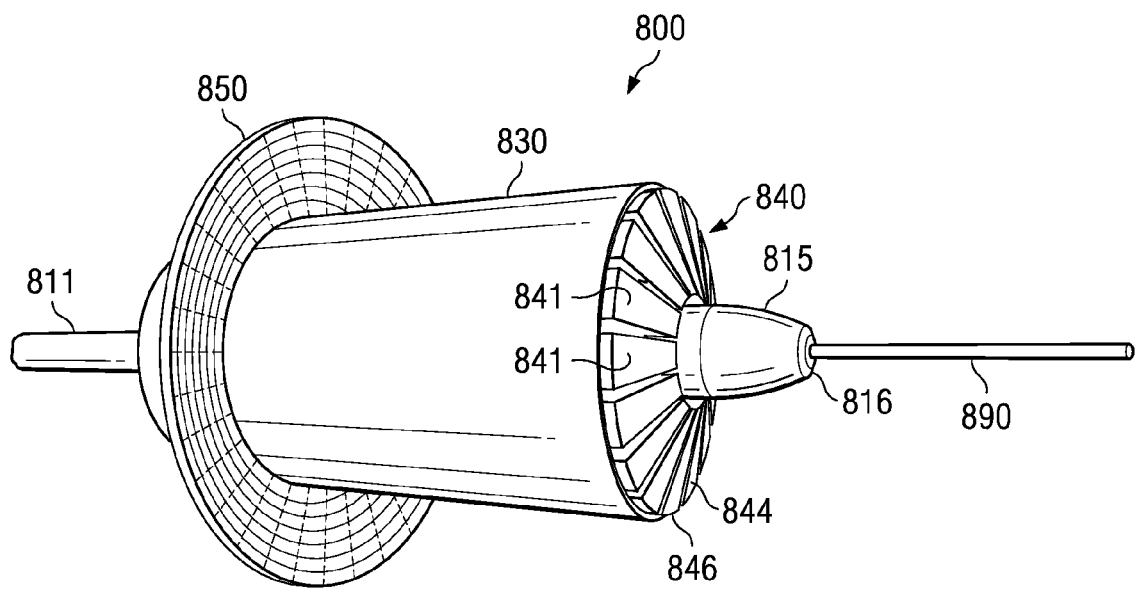
FIG. 11 illustrates the outer hollow body in the process of releasing distal sealing member from its collapsed position.
Figure 11B:
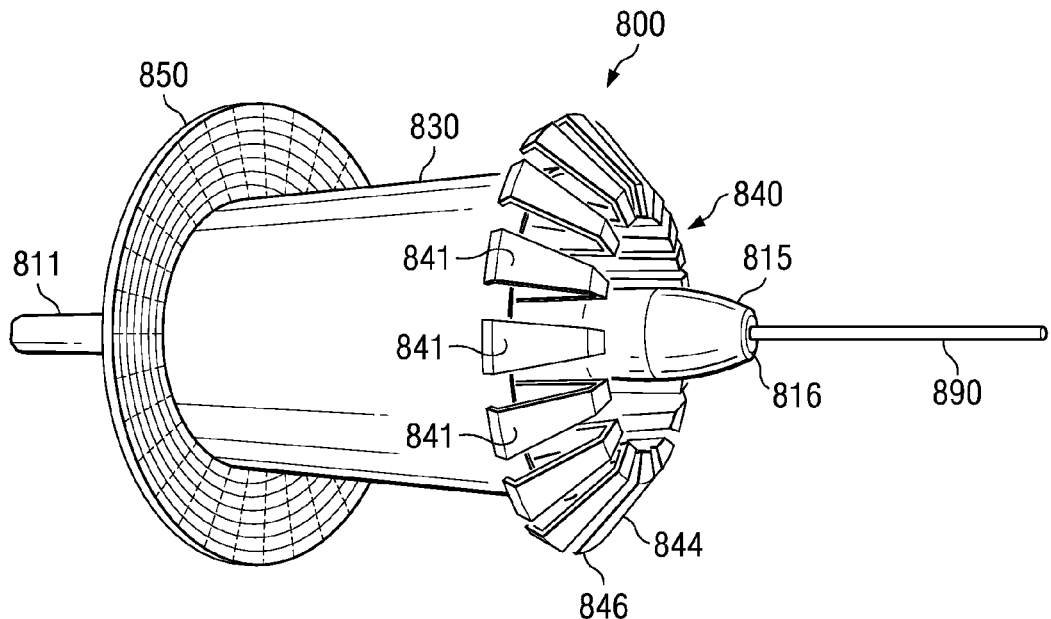
Figure 11C:
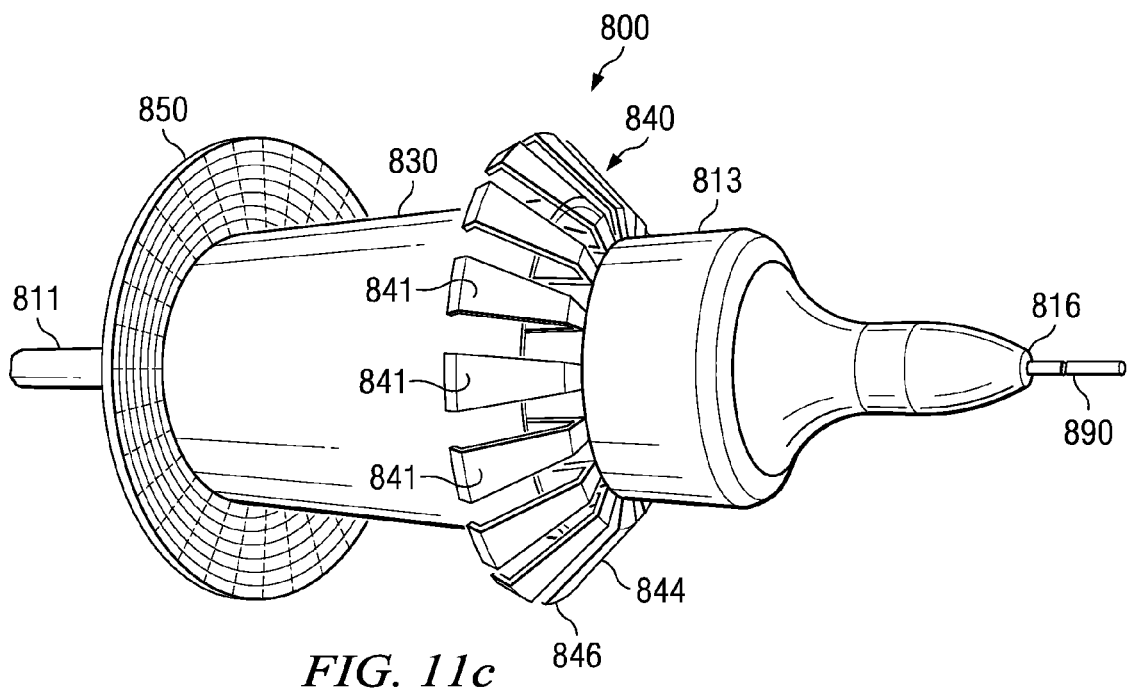

Medial portion 813 of inner body 810 is inserted until proximal sealing member 850 contacts the outer surface of organ. Distal sealing member 840 is held in its compressed position by outer hollow body 830 as shown in FIG. 11A. Once medial portion 813 has been inserted, the surgeon pulls back outer hollow body 830 allowing the ribs 841 of distal sealing member 840 to spring radially outward as seen in FIG. 11B.

Once distal sealing member 840 has been initially uncompressed, inner body 810 is further pushed distally into organ 880. See FIG. 10C & FIG. 8. As medial portion 813 of inner body 810 is pushed inward, axial portions 843 of each rib 841 engage intermediate sheath 820 surrounding medial portion 813. Ribs 841 are further displaced radially outward until distal sealing member 840 reaches its fully expanded position. Furthermore, intermediate sheath 820 slides underneath axial portions of ribs to lock distal sealing member 840 into its expanded position as shown in FIG. 9. That is, intermediate sheath 820 prevents distal sealing member 840 from reverting to its compressed position and maintains distal sealing member 840 in its fully expanded position. Intermediate sheath 820 may comprise a stop or tab located at its proximal end to indicate to surgeon that distal sealing member 840 is fully expanded and locked into position.

Figure 12A:
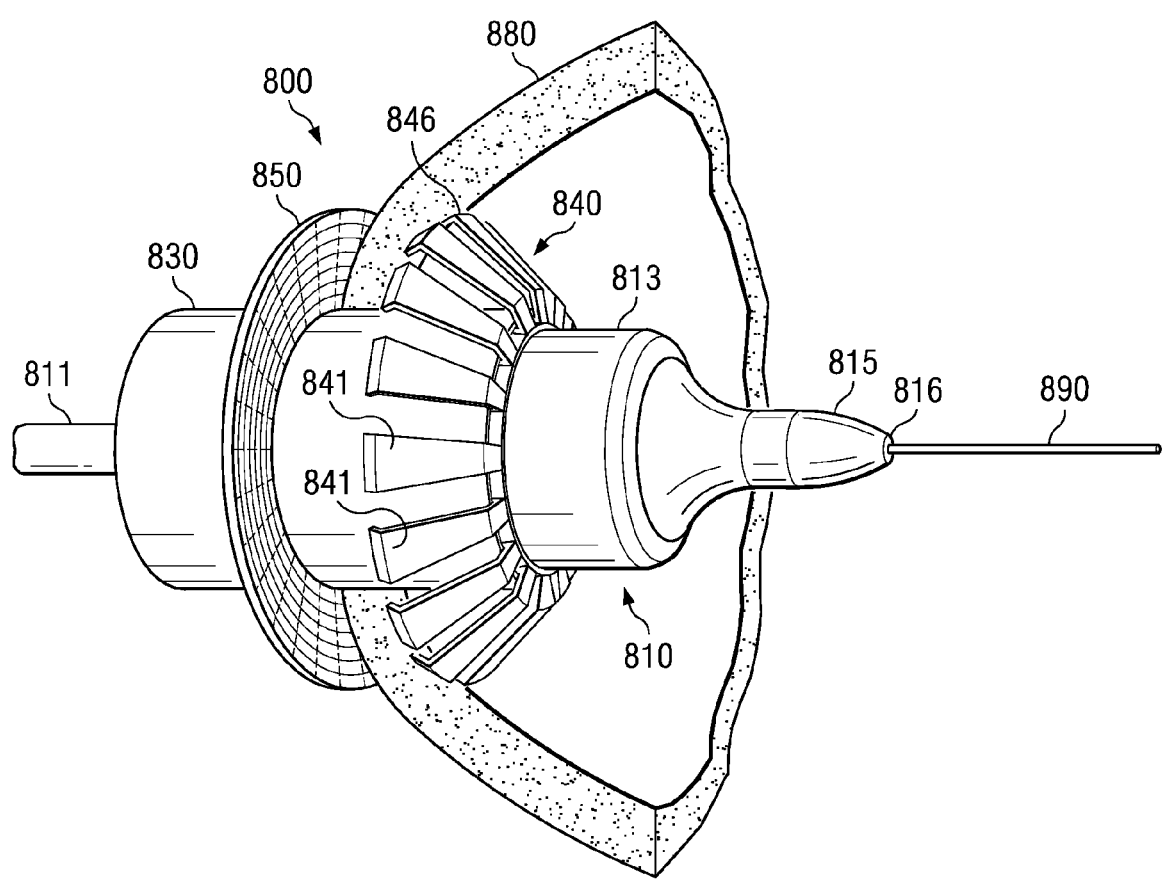
FIG. 12 illustrates the removal of inner body from the other elements of the surgical connector.
Figure 12B:
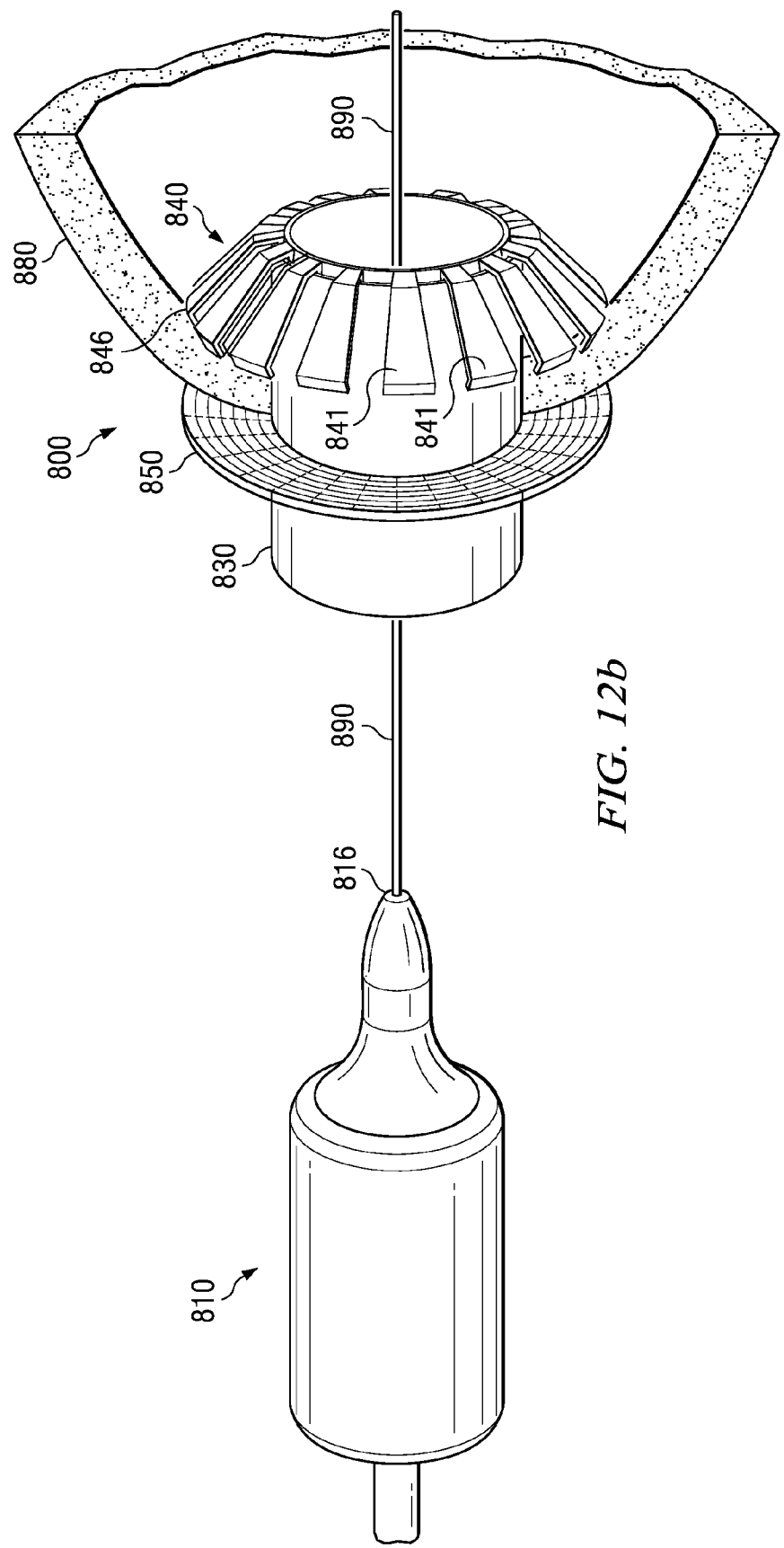

Once distal sealing member 840 is locked into position, surgeon may adjust or tighten proximal sealing member 850 against outer surface of organ to secure a liquid tight seal. The tightening may be accomplished by whatever mechanism is incorporated by the device such as a ratchet mechanism or a screw connection (not shown). Thus, organ wall will be securely clamped between inner and proximal sealing member 830, 850 to form a press-fit type connection. As such, the disclosed surgical connector 800 does not need sutures to be secured to the organ 880. When organ wall is securely clamped by inner and proximal sealing members 830, 850, the surgeon may then pull inner body 810 from intermediate sheath 820 and outer hollow body 830 leaving a secured connector or conduit for attachment of a surgical device as seen in FIG. 12B. In an embodiment, the surgical device is an LVAD, although any suitable surgical device may be attached to surgical connector 800. As surgeon removes inner body 810, the balloon catheter once again serves as a plug to prevent blood loss from the organ.

Balloon-type Catheters for Off-Pump Surgery

Figure 7:
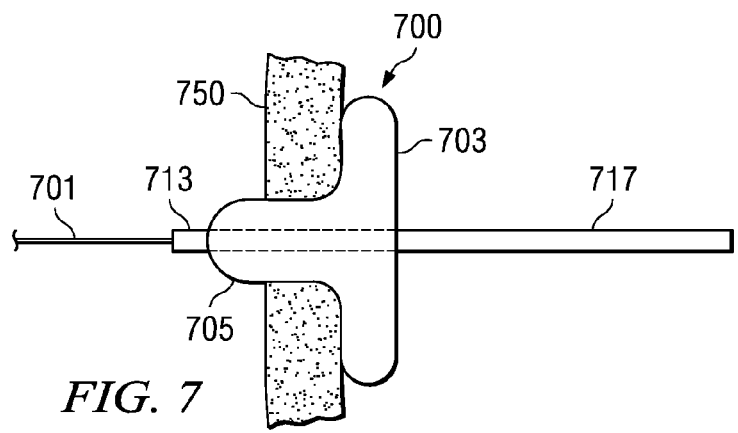
FIG. 7 illustrates an embodiment of a balloon catheter used in a surgical coring system.

The coring system described above is preferably used in conjunction with a balloon-type catheter specifically designed for blocking a cavity in the ventricle. As shown in FIG. 7, the balloon catheter 700 is coaxial with guide wire 701. The inflatable balloon portion of catheter 700 may comprise any shape that is suitable for blocking a hole in the ventricle. In one embodiment, balloon has a frusto-conical shape when inflated. In another embodiment, balloon comprises a seal or cuff portion 403 continuous with a distal projection 705 to form a nipple shaped balloon (FIG. 7). The distal projection 703 is ideally approximately the same diameter as the cored hole while seal portion 705 has a greater diameter than distal portion 705 to form a seal within the ventricle 750. Seal portion may have a convex curvature which closely resembles the curvature of the ventricle. Distal tip of distal projection 705 is preferably bullet shaped to allow catheter to easily slip through and plug cored hole. In addition, the distal tip 713 of catheter body 717 is optimally spaced to prevent coring tool from puncturing balloon.

In yet another embodiment, catheter comprises a mechanically expandable seal (not shown). The advantage of this embodiment is that there would be no danger of puncturing an inflated balloon. It is envisioned that the expandable and collapsible mechanical seal would operate much like an umbrella. The mechanical seal would operate similarly to the expandable sealing member described above. In an embodiment, mechanical seal comprises a collapsible skeleton or frame covered by a non-thrombogenic material. The mechanical seal preferably has a curved aspect to better fit the interior of the ventricle.

An additional embodiment of balloon catheter comprises a low-profile proximal valve (not shown). In a preferred embodiment, proximal valve has the same diameter as the catheter body. Proximal valve is generally a one way valve. That is, proximal valve allows the balloon catheter to be filled with liquid or gas, but maintains pressure within the balloon portion after balloon portion has been inflated. Any suitable valve known to those of skill in the art may be used.

In a particular embodiment, balloon catheter further comprises a proximal catheter portion which is coupled to the proximal valve after balloon inflation such that distal catheter portion and proximal catheter portion form a continuous catheter body. Catheter body preferably has a small diameter, ranging from about 0.01 mm to about 10 mm. It is envisioned that catheter body may act as a guide wire for various surgical devices including without limitation, the coring tool 300 or surgical connector 800. Thus, in an embodiment, balloon catheter 700 and coring tool 300 may be used as part of a surgical coring system without the need for an additional guide wire.

In such an embodiment, balloon catheter does not require a guide wire. Instead, the distal tip of balloon catheter is inserted at the target area of an organ. An incision may optionally be made at the target area to facilitate insertion of balloon catheter. Balloon catheter is inserted into the organ and then inflated by injecting either a fluid or a gas into the balloon. Balloon portion may be inflated by any suitable device such as a pump, injection port, syringe, etc. attached to the proximal valve of balloon catheter. Once balloon portion is inflated, the injection device is removed from proximal valve. Because of the one-way nature of the valve, the balloon portion remains inflated even after the injection device is removed. The proximal portion is then attached to the distal portion through a suitable connection such as a threaded connection forming the continuous catheter body.

It is further envisioned that each of the devices disclosed herein may incorporated as elements of a medical kit. For example, a kit for off-pump connection of an artificial device may comprise the disclosed surgical connector, an embodiment of a balloon catheter as described above, a guide wire, and the disclosed coring tool. The kit may comprise any combination or number of the surgical devices disclosed herein. Furthermore, it is contemplated that any of the methods and apparatuses described herein are not limited to off-pump surgery, but may be used in conjunction with any surgical procedure whether it be on-pump or off-pump.

While embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A surgical device comprising:
   a surgical connector comprising a cylindrical body surrounded by a correspondingly-shaped suture cuff, said surgical connector configured to be sutured to an organ to form a fluid-tight seal between said surgical connector and the organ;
   a suction element configured to be releasably coupled to the cylindrical body of the surgical connector, wherein said suction element has an opening for stabilizing the surgical connector against the surface of the organ by suction; and
   a flexible arm connected to said suction element, wherein said flexible arm is configured to be fixed in a stationary position to hold the surgical connector and the organ in place.

2. The surgical device of claim 1, wherein said suction element is adapted to be releasably coupled to said surgical connector by a friction fitting.

3. The surgical device of claim 1, wherein said suction element is adapted to slidingly fit within said surgical connector.

4. The surgical device of claim 1, wherein said suction element is adapted to slidingly fit around said surgical connector.

5. The surgical device of claim 1, wherein said suction element is adapted to be releasably coupled to said surgical connector by a connection selected from the group consisting of a threaded connection, a bayonet connection, and a snap-fit connection.

6. The surgical device of claim 1, wherein said surgical connector is an apical ventricular assist device connector.

7. The surgical device of claim 1, wherein said flexible arm is connected to said suction element by a hollow member, wherein said hollow member is in fluid communication with said suction element.

8. The surgical device of claim 7, further comprising a vacuum line attached to said hollow member.

9. The surgical device of claim 1, wherein said flexible arm is hollow.

10. The surgical device of claim 9, wherein a vacuum line is attached to the proximal end of said flexible arm such that vacuum is drawn from the suction element through said flexible arm.

11. The surgical device of claim 1, wherein said suction element is detachably attached to said flexible arm.

12. The surgical device of claim 8, wherein said hollow member is attached to said flexible arm by a joint selected from the group consisting of a hinge, a swivel joint, and a ball joint.

13. The surgical device of claim 1, wherein said suction element is tubular.

14. The surgical device of claim 1, wherein said flexible arm comprises a non-resilient, deformable material.

15. The surgical device of claim 1, wherein said suction element comprises a polymeric material.

16. The surgical device of claim 1, wherein said organ is a heart.

17. A surgical device comprising:
    a surgical connector comprising a hollow body surrounded by a suture ring, said suture ring of said surgical connector configured to be sutured to an organ to form a fluid-tight seal between said surgical connector and a surface of the organ;

a suction element releasably coupled to said surgical connector, wherein said suction element has an opening for securing said surgical connector to the surface of the organ by suction; and a flexible arm connected to said suction element, wherein said flexible arm is configured to be locked into a fixed position to stabilize said surgical connector and the organ;

wherein said surgical connector is configured to be fixed in place connected to the organ after the suction element is decoupled from the surgical connector.

18. The surgical device of claim 17, wherein said surgical connector is coaxially coupled to said suction element.

19. The surgical device of claim 17, wherein said surgical connector is adapted to be releasably coupled to said suction element.

20. The surgical device of claim 17, wherein said surgical connector is a ventricular assist device connector.

21. A method comprising:
a) providing a surgical device comprising:
  a flexible arm capable of being fixed in a stationary position, said flexible arm attached to a suction element, wherein said suction element is releasably coupled to a surgical connector;
b) applying a vacuum to said suction element;
c) positioning the suction element releasably coupled to the surgical connector on to the surface of an organ, wherein said surgical connector and said organ are held in place by the vacuum from the suction element;
d) fixing said flexible arm in a desired position to stabilize the organ and the surgical connector; and
(e) suturing the surgical connector to the surface of the organ to form a fluid-tight seal.

22. The method of claim 21, further comprising de-coupling said suction element from said surgical connector, wherein said surgical connector is left attached to said organ.

* * * * *